(12) United States Patent
Nishikata et al.

(10) Patent No.: US 6,740,315 B2
(45) Date of Patent: May 25, 2004

(54) COATED POWDER AND COSMETIC PREPARED BY BLENDING THE SAME

(75) Inventors: Kazuhiro Nishikata, Yokohama (JP); Hirochika Nishimura, Yokohama (JP)

(73) Assignee: Pola Chemical Industries, Inc., Shizuoka (JP)

( * ) Notice: Subject to any disclaimer, the term of this patent is extended or adjusted under 35 U.S.C. 154(b) by 0 days.

(21) Appl. No.: 09/147,861

(22) PCT Filed: Mar. 26, 1997

(86) PCT No.: PCT/JP97/01025
§ 371 (c)(1),
(2), (4) Date: Mar. 17, 1999

(87) PCT Pub. No.: WO98/11865
PCT Pub. Date: Mar. 26, 1998

(65) Prior Publication Data
US 2003/0035883 A1 Feb. 20, 2003

(30) Foreign Application Priority Data
Sep. 17, 1996 (JP) ............................................. 8-266680

(51) Int. Cl.$^7$ .......................... A61K 7/021; A61K 9/14; A61K 9/16; C09C 1/36; C08K 3/00

(52) U.S. Cl. .................... 424/63; 106/287.19; 106/436; 106/450; 106/481; 424/69; 424/401; 424/489; 424/490; 427/402; 514/770

(58) Field of Search .......................... 424/401, 63, 69, 424/489, 490; 427/402; 514/770; 106/287.19, 436, 450, 481

(56) References Cited

U.S. PATENT DOCUMENTS 5,246,780 A * 9/1993 Farer et al.

* cited by examiner

Primary Examiner—Shelley A. Dodson
Assistant Examiner—Marina Lamm
(74) Attorney, Agent, or Firm—Knobbe, Martens, Olson & Bear, LLP

(57) ABSTRACT

Coated powder is obtained by applying a material having a refractive index of 1.9 to 3.1 to powder having a refractive index of 1.3 to 1.8 as a core and further applying a material having a refractive index of 1.3 to 1.8 to the coated core. When this powder is used for cosmetics or paints, natural coloring can be accomplished without deteriorating lightness because a screening effect is not high.

9 Claims, No Drawings

COATED POWDER AND COSMETIC PREPARED BY BLENDING THE SAME

This is a 35 U.S.C. §371 application of PCT/JP97/01025, filed Mar. 26, 1997.

TECHNICAL FIELD

The present invention relates to a coated powder, and more particularly relates to the coated powder that accomplishes natural coloring without deteriorating lightness when it is used as cosmetics or paints, and to a cosmetic prepared by blending the coated powder.

BACKGROUND ART

Conventionally, silica, titania dioxide or silica having a metal oxide such as titanium coated on the surface thereof has been known as pigments for cosmetics or paints. However, although titanium dioxide has high screening effect, there has been the problem that if it is used in a large amount, unnatural whiteness is obtained or lightness decreases, thereby it is difficult to obtain natural coloring.

DISCLOSURE OF THE INVENTION

The present invention has been made in view of the above circumstances, and has an object to provide a powder that accomplishes natural coloring without deteriorating lightness, and a cosmetic prepared by blending the same.

As a result of extensive investigations in view of the above existing circumstances, the present inventors have found that if a material having a refractive index of 1.9 to 3.1 is applied to a powder having a refractive index of 1.3 to 1.8 as a core, and a material having a refractive index of 1.3 to 1.8 is further applied thereto, linear transmission property of light at each wavelength can be freely adjusted by controlling a thickness of each coating layer; and since the total transmission amount can be maintained nearly 100% without substantially receiving influence of the coating thickness, when used as pigments for cosmetics, paints, or the like, a screening effect is not strong and lightness is not deteriorated, thereby natural coloring can be accomplished.

That is, the present invention provides a coated powder comprising (A) powder having a refractive index of 1.3 to 1.8 as a core, (B) a coating layer of a material having a refractive index of 1.9 to 3.1 on the powder (A), and (C) a coating layer of a material having a refractive index of 1.3 to 1.8 on the coating layer (B). The coated powder of the present invention enables linear transmittance of light to be adjusted according to the purpose of use, has a high total transmission amount of light, and does not substantially deteriorate lightness.

Further, the present invention provides a cosmetic prepared by blending the above-mentioned coated powder.

The present invention is described in detail below.

The coated powder of the present invention can be prepared by applying a material having a refractive index of 1.9 to 3.1 and a material having a refractive index of 1.3 to 1.8 to a powder having a refractive index of 1.3 to 1.8 as a core in that order with known methods such as a sol-gel method and a spray drying method.

The powder used as a core may have plate-like shape, spherical shape or indeterminate shape, but spherical shape is preferable in order to allow light to diffuse and transmit uniformly. Particle size of the powder used as a core may appropriately be adjusted depending on the conditions such as particle size of the desirable coated powder and weight ratio between the powder as a core and a material which is applied to the powder as a core as mentioned below. In general, the particle size of the powder as a core is preferably 0.05 to 45 $\mu$m, and particularly preferably 0.3 to 28 $\mu$m, although varying depending on the shape of the powder as a core. Further, the refractive index of the powder as a core is preferably 1.3 to 1.8, and particularly preferably 1.5 to 1.6. Examples of a material that can be used as the powder for a core include silica (refractive index n=about 1.54422), alumina (refractive index n=about 1.76–1.77), calcium carbonate (refractive index n=about 1.6585), and the like, and silica is preferable from the point of transmittance.

The material that is first applied to the powder as a core to form a first layer preferably has a refractive index of 1.9 to 3.1, and particularly preferably 2.1 to 2.6. Examples of the material that is first applied to the powder as a core to form a first layer include titania (refractive index n=about 2.493–2.586), zirconia (refractive index n=about 2.13, 2.19 or 2.20), and the like. The coating amount of this first layer can be adjusted depending on applications of the coated powder, but generally it may be about 1 to 50% by weight, and preferably about 5 to 30% by weight, based on the total amount of the coated powder. If the coating amount is less than 1% by weight, a screening effect is not sufficient, and if it exceeds 50% by weight, lightness lowers, which are not preferable.

The material that is further applied to the first layer on the core powder to form a second layer preferably has a refractive index of 1.3 to 1.8, and particularly preferably 1.5 to 1.6. Examples of the material for forming the second layer include silica, alumina, calcium carbonate, and the like, and the silica is preferable from the point of transmittance. The coating amount of this second layer can appropriately be adjusted depending on applications of the coated powder, but generally it may be about 1 to 30% by weight, and preferably about 2 to 10% by weight, based on the total amount of the coated powder. If the coating amount is less than 1% by weight, the total transmission amount of light decreases, and lightness does not increase, and even if it is applied in an amount exceeding 30% by weight, further improvement is not obtained in the effect of increasing lightness, which is not economical.

The coated powder of the present invention generally has a particle size of preferably 0.1 to 50 $\mu$m, and particularly preferably 0.4 to 30 $\mu$m, although depending on its shape. Even if the particle size is outside the above-mentioned range, the effect by the coated powder of the present invention can be obtained. However, if the particle size is within this range, it is easier to handle as pigments used for cosmetics, paints, or the like, and when it is blended into cosmetics, texture when applied is better.

In order to obtain such a coated powder, for example, an alkoxysilane is subjected to hydrolysis by addition of ammonia to produce spherical silica particles, the particles are then introduced into a titianium alkoxide solution, and hydrolysis is conducted to form a coating layer of hydrolyzate of titanium alkoxide on the surface, followed by burning, or the like, thereby forming a coating layer as the first layer. This coated powder is further introduced into an alkoxysilane solution, the alkoxysilane is hydrolyzed to form the second layer, followed by burning, thereby producing the coated powder of the present invention. Formation of the second layer can also be conducted by a method in which an alkoxysilane solution is sprayed to the powder having the first layer, then the obtained powder is heated and dried. Further, commercially available silica powder can be used as the powder of starting material. For example, true spherical silica powder produced by the process described in Japanese Patent Application Laid-open No. 61-270201 and the like are exemplified.

The coated powder of the present invention can be blended into cosmetics, paints, or the like. The blending amount of the coated powder may be appropriately adjusted depending on the purpose of cosmetics, paints, or the like.

In the cosmetic of the present invention containing the above-mentioned coated powder, form and application thereof are not particularly limited, and the form may be, for example, a solution-form, a milky lotion-form, a cream-form, an aqueous gel-form or the like. The application thereof includes foundation, control color, make-up base, eye color, face lotion, face milky lotion, cheek color, lip color, and the like. In addition to the above-mentioned coated powder, the cosmetic of the present invention can contain various components generally used in cosmetics such as aqueous component, oily component, surface active agent, moisturizer, thickener, coloring material, perfume, antioxidant, pH modifier, chelating agent, preservative, ultraviolet inhibitor, anti-inflammatory agent, whitening agent and powder other than the coated powder of the present invention.

The cosmetic of the present invention can be prepared in the same manner as in the ordinary cosmetics except for blending the coated powder.

BEST MODE FOR CARRYING OUT THE INVENTION

The coated powder of the present invention is explained by referring to the following examples.

EXAMPLE 1

2 wt % aqueous ammonia was gradually added dropwise to a solution of 10 wt % monomethyl-triethoxysilane in ethanol, and the resulting mixture was stirred for 3 hours to produce spherical silica particle (particle size: 0.8 $\mu$m, and about 0.55 $\mu$m after burning). This particle was filtered off and washed with water, and then heated and dried at 300° C. for 4 hours. The particle was cooled to the room temperature, and then introduced into a solution of 3 wt % titanium isopropoxide in isopropanol. After that, while stirring the resulting mixture under nitrogen atmosphere, 10 ml of isopropanol containing 5% water was gradually added dropwise thereto, thereby depositing hydrolyzate of titanium isoproproxide on the surface of the particle. After filtration, the particle was washed with water, and then heated and dried at 300° C. for 4 hours. This powder was further introduced into a solution of 10 wt % tetraethoxysilane in ethanol, and 1N aqueous hydrochloric acid was gradually added dropwise thereto. The resulting mixture was stirred for one day-and-night to form a silica coating layer on the surface of the particle. The powder finally obtained was burned at 800° C. for 4 hours to obtain a coated powder (I). Weight ratio of silica and titania was obtained from a peak intensity ratio originated from titanium dioxide ($TiO_2$) by X ray diffraction in each coating stage. As a result, the ratio of silica (powder as a forming core):titania (first layer) silica (second layer) of the coated powder (I) was 70:20:10. Further, the particle size of the coated powder (I) was about 0.6 $\mu$m after burning.

EXAMPLE 2

True spherical silica resin powder (Tospearl 120, a product of Toshiba Silicone Co., Ltd.) was placed in an electric furnace, and temperature was risen from the room temperature to 1000° C. at a rate of 20° C. per minute. After the powder was burned at this temperature for 6 hours, electric power was off, and the powder was spontaneously cooled to the room temperature to obtain true spherical silica powder (particle size: 0.85 $\mu$m). This silica powder was introduced into a solution of 5 wt % zirconium tetra-n-propoxide in isopropanol, and hydrolysis was conducted while gradually adding dropwise isopropanol containing 5% water under argon atmosphere. The powder obtained was burned at 800° C. to obtain a zirconia-coated powder. This zirconia-coated powder was introduced into a solution of 10 wt % tetraethoxysilane in ethanol, and 1N aqueous hydrochloric acid was gradually added dropwise, followed by stirring for one day-and-night, thereby forming a silica coating layer on the surface. The powder finally obtained was burned at 800° C. for 4 hours to obtain a coated powder (II). Weight ratio of silica and zirconia was obtained from a peak intensity ratio originated from zirconium dioxide ($ZrO_2$) by X ray diffraction in each coating stage of the production in the same manner as in Example 1. As a result, the ratio of silica (powder as a forming core):zirconia (first layer):silica (second layer) of the coated powder (II) was 80:10:10. Further, the particle size of the coated powder (II) was about 0.9 $\mu$m after burning.

EXAMPLE 3

2 wt % aqueous ammonia was gradually added dropwise to a solution of 10 wt % monomethyl-triethoxysilane in ethanol, and the resulting mixture was stirred for 3 hours to produce spherical silica particle (particle size: 0.8 $\mu$m). This particle was filtered off and washed with water, and then heated and dried at 300° C. for 4 hours. The particle was cooled to the room temperature, and then introduced into a solution of 3 wt % titanium isopropoxide in isopropanol. After that, while stirring the resulting mixture under nitrogen atmosphere, 10 ml of isopropanol containing 5% water was gradually added dropwise thereto, thereby depositing hydrolyzate of titanium isopropoxide hydrolyzate on the surface of the particle. After filtration, the particle was washed with water, and then heated and dried at 300° C. for 4 hours. This powder was further introduced into a solution of 10 wt % tetraethoxysilane in ethanol, and then 1N aqueous hydrochloric acid was gradually added dropwise thereto. The resulting mixture was stirred for one day-and-night to form a silica coating layer on the surface of the particle. The powder finally obtained was burned at 800° C. for 4 hours to obtain a coated powder (III). Weight ratio of silica and titania was obtained from a peak intensity ratio originated from titanium dioxide ($TiO_2$) by X ray diffraction in each coating stage of the production in the same manner as in Example 1. As a result, the ratio of silica (powder as a forming core):titania (first layer):silica (second layer) of the coated powder (III) was 85:5:10. Further, the particle size of the coated powder (III) was about 0.6 $\mu$m after burning.

EXAMPLE 4

2 wt % aqueous ammonia was gradually added dropwise to a solution of 10 wt % monomethyl-triethoxysilane in ethanol, and the resulting mixture was stirred for 3 hours to produce spherical silica particle (particle size: 0.8 $\mu$m). This particle was filtered off and washed with water, and then heated and dried at 300° C. for 4 hours. The particle was cooled to the room temperature, and then introduced into a solution of 3 wt % titanium isopropoxide in isopropanol. After that, while stirring the resulting mixture under nitrogen atmosphere, 10 ml of isopropanol containing 5% water was gradually added dropwise thereto, thereby depositing hydrolyzate of titanium isopropoxide on the surface of the particle. After filtration, the particle was washed with water, and then heated and dried at 300° C. for 4 hours. This powder was further introduced into a solution of 10 wt % tetraethoxysilane in ethanol, and 1N aqueous hydrochloric acid was gradually added dropwise thereto. The resulting mixture was stirred for one day-and-night to form a silica coating layer on the surface of the particle. The powder finally obtained was burned at 800° C. for 4 hours to obtain a coated powder (IV). Weight ratio of silica and titania was obtained from a peak intensity ratio originated from titanium dioxide ($TiO_2$) by X ray diffraction in each coating stage of the production in the same manner as in Example 1. As a result, the ratio of silica (powder as a forming core):titania (first layer) silica (second layer) of the coated powder (IV) was 87.5:2.5:10. Further, the particle size of the coated powder (IV) was about 0.6 µm after burning.

Table 1 shows light transmission data of the coated powders obtained in the Examples and the conventionally known powders as the Comparative Examples at 400, 500, 600 and 700 nm. Linear transmittance is obtained by receiving light passing through the powder at the immediate back thereof and measuring the amount of transmitted light. Total transmittance is obtained by measuring the amount of light transmitted while scattering in each direction, using an integrating sphere.

TABLE 1

|  | Linear transmittance (nm) | | | | Total transmittance (nm) | | | |
| --- | --- | --- | --- | --- | --- | --- | --- | --- |
|  | 400 | 500 | 600 | 700 | 400 | 500 | 600 | 700 |
| Comparative Example 1 Monodisperse spherical silica (0.55 µ) | 73 | 78 | 82 | 86 | 100 | 100 | 99 | 99 |
| Comparative Example 2 Monodisperse spherical silica (1.4 µ) | 58 | 66 | 69 | 72 | 100 | 100 | 100 | 100 |
| Comparative Example 3 Silicic anhydride *1 | 8 | 9 | 10 | 12 | 93 | 93 | 93 | 93 |
| Comparative Example 4 Titania-coated silica *2 | 6 | 8 | 11 | 15 | 77 | 82 | 83 | 85 |
| Comparative Example 5 Titania-coated silica *3 | 76 | 81 | 84 | 88 | 99 | 98 | 97 | 97 |
| Comparative Example 6 Titanium dioxide *4 | 3 | 12 | 24 | 36 | 57 | 69 | 77 | 81 |
| Comparative Example 7 Titania-coated sericite *5 | 18 | 26 | 32 | 39 | 81 | 84 | 84 | 85 |
| Comparative Example 8 Iron oxide & silica coated mica *6 | 21 | 30 | 40 | 47 | 58 | 74 | 88 | 89 |
| Comparative Example 9 Iron oxide & silica coated mica *7 | 22 | 30 | 40 | 47 | 55 | 72 | 87 | 87 |
| Coated powder obtained in Example 1 | 15 | 21 | 28 | 36 | 93 | 95 | 94 | 95 |
| Coated powder obtained in Example 2 | 20 | 27 | 34 | 42 | 98 | 99 | 98 | 98 |
| Coated powder obtained in Example 3 | 40 | 50 | 58 | 66 | 99 | 99 | 99 | 99 |

TABLE 1-continued

|  | Linear transmittance (nm) | | | | Total transmittance (nm) | | | |
| --- | --- | --- | --- | --- | --- | --- | --- | --- |
|  | 400 | 500 | 600 | 700 | 400 | 500 | 600 | 700 |
| Coated powder obtained in Example 4 | 53 | 62 | 69 | 73 | 99 | 99 | 99 | 99 |

*1: Silica microbead 1500 (Shokubai Kasei Kogyo K.K.)
*2: Silica coated with titania at 20%
*3: Silica coated with titania at 5%
*4: Anatase-type titanium dioxide (Tiepeek A-100, Ishihara Sangyo Kaisha, Ltd.)
*5: Sericite coated with titania at 30%
*6: Mica coated with a mixture of iron oxide and silica at 2% and 10%
*7: Mica coated with a mixture of iron oxide and silica at 2% and 50%

As it is apparent from the results of Table 1, the respective powders of the Examples can adjust the linear transmittance at each wavelength by the weight ratio of silica (powder as a forming core):titania or zirconia (first layer):silica (second layer) of the coated powder, and the amount of total light transmission shows the value near 100%. This characteristic is not seen in other single component powders or one-layer coated powders.

Next, foundations having the compositions shown in Table 2 were prepared using those powders. The results obtained by measuring linear transmittance and total transmittance of each foundation are shown in Table 3.

TABLE 2

|  | Comparative Example | | | | | | | | | Example | | | |
| --- | --- | --- | --- | --- | --- | --- | --- | --- | --- | --- | --- | --- | --- |
|  | 10 | 11 | 12 | 13 | 14 | 15 | 16 | 17 | 18 | 5 | 6 | 7 | 8 |
| Powder of Comparative Example 1 | 40 | | | | | | | | | | | | |
| Powder of Comparative Example 2 | | 40 | | | | | | | | | | | |
| Powder of Comparative Example 3 | | | 40 | | | | | | | | | | |
| Powder of Comparative Example 4 | | | | 40 | | | | | | | | | |
| Powder of Comparative Example 5 | | | | | 40 | | | | | | | | |
| Powder of Comparative Example 6 | | | | | | 40 | | | | | | | |
| Powder of Comparative Example 7 | | | | | | | 40 | | | | | | |
| Powder of Comparative Example 8 | | | | | | | | 40 | | | | | |
| Powder of Comparative Example 9 | | | | | | | | | 40 | | | | |
| Powder of Example 1 | | | | | | | | | | 40 | | | |
| Powder of | | | | | | | | | | | 40 | | |

TABLE 2-continued

| | Comparative Example | | | | | | | | Example | | | |
|---|---|---|---|---|---|---|---|---|---|---|---|---|
| | 10 | 11 | 12 | 13 | 14 | 15 | 16 | 17 | 18 | 5 | 6 | 7 | 8 |
| Example 2 | | | | | | | | | | | | | |
| Powder of Example 3 | | | | | | | | | | | 40 | | |
| Powder of Example 4 | | | | | | | | | | | | | 40 |
| Yellow iron oxide | | | | | | | 3 | | | | | | |
| Red iron oxide | | | | | | | 1 | | | | | | |
| Methyl paraben | | | | | | | 0.2 | | | | | | |
| Talc | | | | | | | 20.8 | | | | | | |
| Sericite | | | | | | | 20 | | | | | | |
| Titanium oxide | | | | | | | 5 | | | | | | |
| Dimethyl polysiloxane | | | | | | | 10 | | | | | | |

TABLE 3

| | Linear transmittance (nm) | | | | Total transmittance (nm) | | | |
|---|---|---|---|---|---|---|---|---|
| | 400 | 500 | 600 | 700 | 400 | 500 | 600 | 700 |
| Comparative Example 10 | 60 | 65 | 70 | 70 | 90 | 92 | 92 | 94 |
| Comparative Example 11 | 55 | 62 | 67 | 67 | 90 | 92 | 92 | 94 |
| Comparative Example 12 | 10 | 16 | 16 | 24 | 87 | 90 | 91 | 90 |
| Comparative Example 13 | 8 | 10 | 20 | 26 | 60 | 62 | 65 | 68 |
| Comparative Example 14 | 59 | 70 | 72 | 75 | 86 | 89 | 90 | 91 |
| Comparative Example 15 | 2 | 10 | 22 | 25 | 50 | 53 | 57 | 66 |
| Comparative Example 16 | 10 | 16 | 17 | 25 | 50 | 53 | 55 | 63 |
| Comparative Example 17 | 10 | 15 | 18 | 26 | 51 | 53 | 55 | 62 |
| Comparative Example 18 | 9 | 16 | 15 | 23 | 45 | 55 | 68 | 68 |
| Example 5 | 10 | 15 | 19 | 28 | 82 | 85 | 87 | 89 |
| Example 6 | 15 | 20 | 22 | 29 | 86 | 89 | 90 | 90 |
| Example 7 | 30 | 38 | 41 | 44 | 86 | 90 | 92 | 90 |
| Example 8 | 47 | 52 | 63 | 60 | 87 | 91 | 93 | 91 |

From the results shown in Table 3, it became apparent that even when the coated powder of the present invention is applied to a foundation, its characteristics are maintained and the total lightness is not decreased.

INDUSTRIAL APPLICABILITY

The coated powder of the present invention can adjust the amount of transmitted light in linear direction by the compositional ratio of components, and also the total transmission amount maintains nearly 100% even in any wavelength region. This characteristic can be maintained even when applied to cosmetics or paints. For this reason, lightness of cosmetics, paints, or the like after coating does not substantially deteriorate. Thus the coated powder is extremely useful.

What is claimed is:

1. A coated powder comprising (A) powder having a refractive index of 1.3 to 1.8 as a core, (B) a coating layer of a material having a refractive index of 1.9 to 3.1 on the powder (A), and (C) a coating layer of a material having a refractive index of 1.3 to 1.8 on the coating layer (B), wherein an amount of the coating layer (C) is 1 to 30% by weight based on the total amount of the coated powder.

2. The coated powder as claimed in claim 1, wherein the amount of the coating layer (B) consisting of the material having a refractive index of 1.9 to 3.1 is 1 to 50% by weight based on the total amount of the coated powder.

3. The coated powder as claimed in claim 1, wherein the material having a refractive index of 1.3 to 1.8 is silica, and the material having a refractive index of 1.9 to 3.1 id titania and/or zirconia.

4. Thew coated powder as claimed in claim 1 wherein the powder as a core has a spherical shape.

5. A cosmetic comprising a pigment composed of a coated powder as claimed in claim 1, and a cosmetically acceptable medium.

6. A method of producing a coated powder wherein a core powder is coated with at least first and second coating layers, said coated powder permitting nearly 100% total light transmission, the core powder having a refractive index of 1.3 to 1.8, the first coating layer of a material having a refractive index of 1.9 to 3.1, the second coating layer of a material having a refractive index of 1.3 to 1.8, said method comprising the steps of:

designing composition of the coated powder by determining a quantity of the first coating layer and a quantity of the second coating layer based on a correlation between the degree of linear transmission and the quantity of each layer, wherein the quantity of the second coating layer is 1 to 30% by weight based on the total amount of the coated powder, to impart a predetermined degree of linear light transmission;

forming the first coating layer in the determined quantity on the core powder; and forming the second coating layer in the determined quantity on the first coating layer formed on the core powder.

7. A method of applying natural coloring on a surface by using a coated powder, comprising the steps of:

designing composition of the coated powder wherein a core powder is coated with at least first and second coating layers, by determining a quantity of the first coating layer and a quantity of the second coating layer based on a correlation between the degree of linear transmission and the quantity of each layer, wherein the quantity of the second coating layer is 1 to 30% by weight based on the total amount of the coated powder, to impart a predetermined degree of linear light transmission, said coated powder permitting nearly 100% total light transmission, the core powder having a refractive index of 1.3 to 1.8, the first coating layer of a material having a refractive index of 1.9 to 3.1, the second coating layer of a material having a refractive index of 1.3 to 1.8; and applying the coated powder on the surface.

8. The coated powder as claimed in claim 1, wherein an amount of the coating layer (C) consisting of the material having a refractive index of 1.3 to 1.8 is 2 to 10% by weight based on the total amount of the coated powder.

9. The coated powder as claimed in claim 1, wherein an amount of the coating layer (B) consisting of the material having a refractive index of 1.9 to 3.1 is 5 to 30% by weight based on the total amount of the coated powder.

* * * * *